United States Patent [19]

van Loveren et al.

[11] Patent Number: 4,532,357

[45] Date of Patent: Jul. 30, 1985

[54] PROCESS FOR PRODUCING 1,1-DIMETHYL-3-INDANONES, PRODUCTS PRODUCED THEREBY AND ORGANOLEPTIC USES THEREOF

[75] Inventors: Augustinus G. van Loveren, Rye, N.Y.; Mark A. Sprecker, Sea Bright, N.J.; Patrick Whelan, Matawan, N.J.; Marie R. Hanna, Hazlet, N.J.

[73] Assignee: International Flavors & Fragrances Inc., New York, N.Y.

[21] Appl. No.: 613,570

[22] Filed: May 24, 1984

[51] Int. Cl.$^3$ .......................... C07C 49/15; A61K 7/46
[52] U.S. Cl. .................... 568/327; 252/522 R; 252/8.6; 252/89.1; 252/108; 568/321
[58] Field of Search ................ 568/321, 327; 252/522 R, 8.6, 89.1, 108

[56] References Cited

U.S. PATENT DOCUMENTS

| | | | |
|---|---|---|---|
| 1,789,924 | 1/1931 | Binapfl et al. | 568/321 |
| 2,912,462 | 11/1959 | Goldstein et al. | 568/327 |
| 3,078,319 | 2/1963 | Wood | 568/327 |
| 3,422,147 | 1/1969 | Fenton | 568/321 |
| 3,509,215 | 4/1970 | Wood et al. | 568/327 |
| 3,847,993 | 11/1974 | Hall et al. | 568/327 |
| 4,175,098 | 11/1979 | Miyukami et al. | 568/321 |

FOREIGN PATENT DOCUMENTS 32-53768 1/1956 Japan .................. 568/327

OTHER PUBLICATIONS

Harms et al., Chem. Abst., vol. 77, #101284r, (1972).
Ferrero et al., Chem. Abst., vol. 54, #14202g, (1960).
Buu-Hoi et al., Bull Chem. Soc. Fr., pp. 812–816, (1947).
Hoy et al., Canadian J. Chem., vol. 43, pp. 1306–1317, (1965).
Arctander, "Perfume and Flavor Chemicals (Aroma Chemicals)", vol. II, Monograph 1791, (1969).

Primary Examiner—James H. Reamer
Attorney, Agent, or Firm—Arthur L. Liberman

[57] ABSTRACT

Described is a process for producing 1,1-dimethyl-3-indanones defined according to the structure:

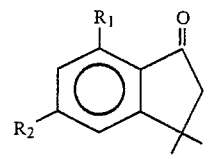

wherein $R_1$ and $R_2$ are the same or different and each represents hydrogen or methyl with the proviso that at least one of $R_1$ and $R_2$ methyl, products produced thereby and organoleptic uses thereof in augmenting or enhancing the aroma of perfume compositions, perfumed articles and colognes.

17 Claims, 9 Drawing Figures

GLC PROFILE FOR EXAMPLE II. CRUDE

GLC PROFILE FOR EXAMPLE I. CRUDE

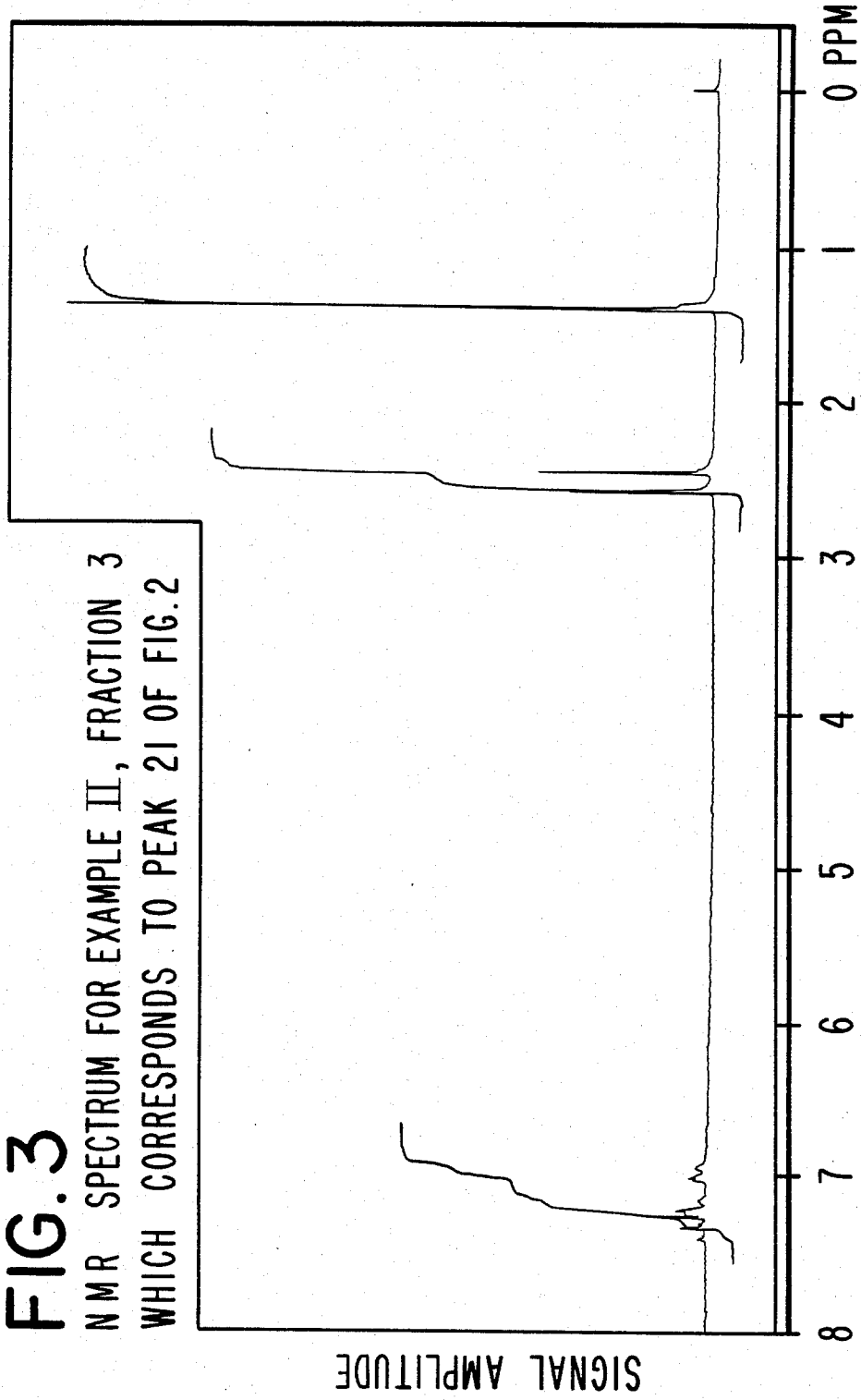
FIG. 3 NMR SPECTRUM FOR EXAMPLE II, FRACTION 3 WHICH CORRESPONDS TO PEAK 21 OF FIG. 2

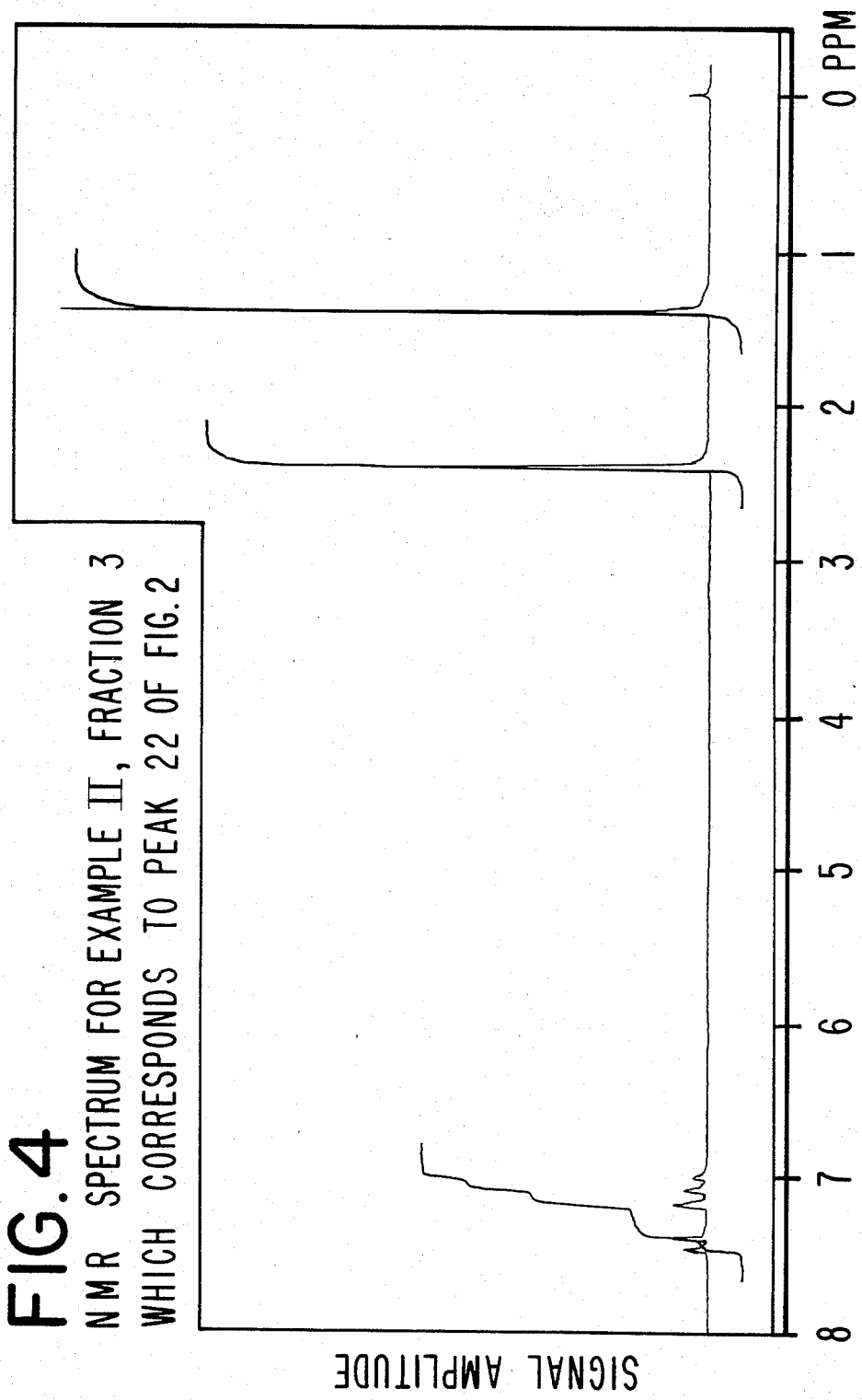
FIG. 4 NMR SPECTRUM FOR EXAMPLE II, FRACTION 3 WHICH CORRESPONDS TO PEAK 22 OF FIG. 2

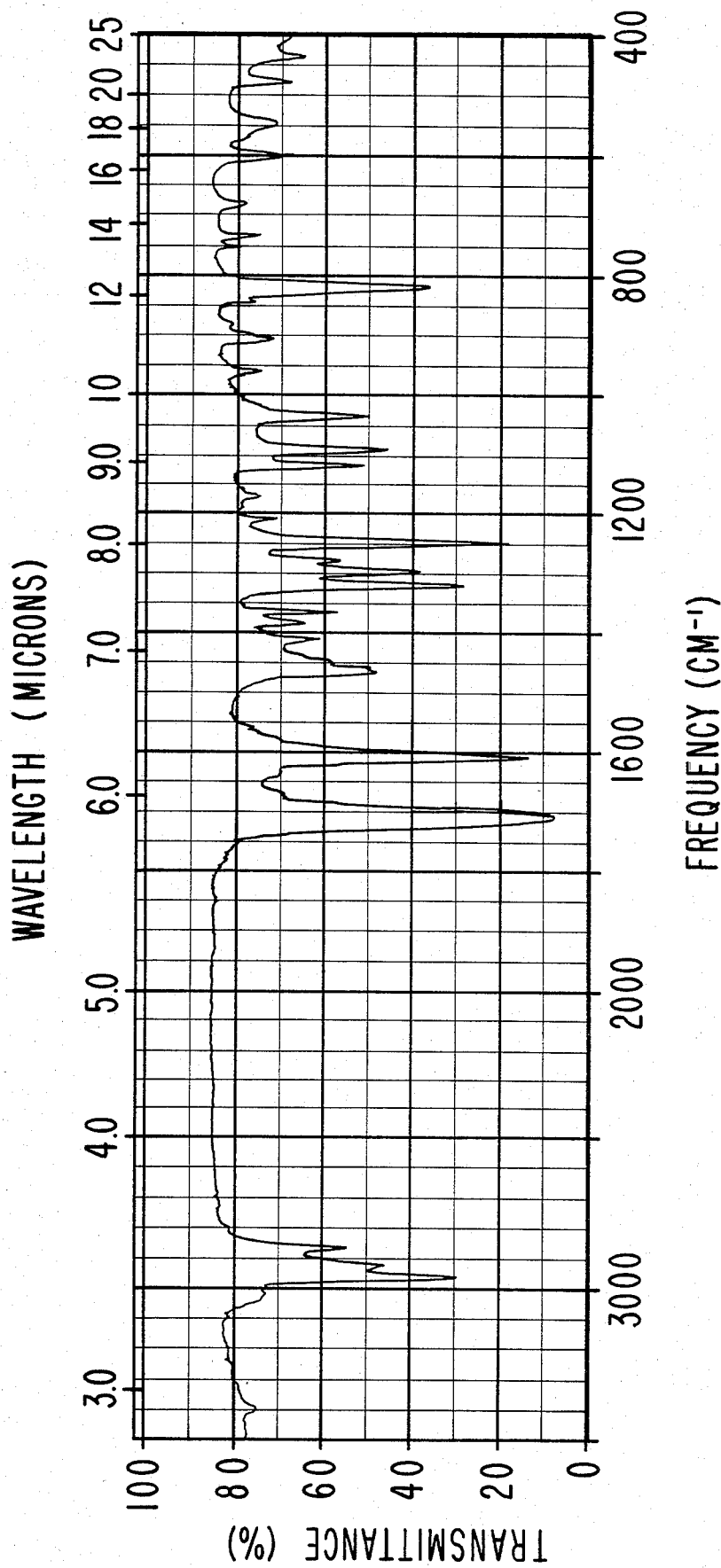

GLC PROFILE FOR EXAMPLE IV. CRUDE

GLC PROFILE FOR EXAMPLE III. CRUDE

NMR SPECTRUM FOR EXAMPLE IV.

IR SPECTRUM FOR EXAMPLE IV.

PROCESS FOR PRODUCING 1,1-DIMETHYL-3-INDANONES, PRODUCTS PRODUCED THEREBY AND ORGANOLEPTIC USES THEREOF

BACKGROUND OF THE INVENTION

The instant invention relates to 1,1-dimethyl-3-indanones defined according to the structure:

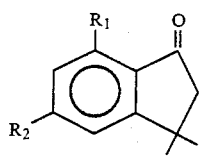

wherein $R_1$ and $R_2$ are the same or different and each represents hydrogen or methyl with the proviso that at least one of $R_1$ and $R_2$ is methyl, a process for preparing same and uses of same in augmenting or enhancing the aroma of perfume compositions, perfumed articles and colognes.

Inexpensive chemical compounds which can provide intense and long lasting leathery, amber, honey-like, orange flower, saffron-like, dried fruit-like, tobacco, woody, fruity and ozoney aromas with leathery, amber, orange flower absolute-like topnotes are highly desirable in the art of perfumery. Many of the natural materials which provide such fragrances and contribute such desired nuances to perfumery compositions are high in cost, unobtainable at times, vary in quality from one batch to another and/or are generally subject to the usual variations of natural products.

There is, accordingly, a continuing effort to find synthetic materials which will replace, enhance or augment the fragrance notes provided by natural essential oils or compositions thereof. Unfortunately, many of the synthetic materials either have the desired nuances only to a relatively small degree or they contribute undesirable or unwanted odor to the compositions.

Bicyclic ketones are known for use in perfumery in the prior art. Thus, Arctander, "Perfume and Flavor Chemicals (Aroma Chemicals)" 1969, at monograph number 1791 and U.S. Pat. No. 2,912,462 issued on Nov. 10, 1959 discloses the compound having the structure:

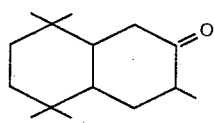

as having a dry, woody, amber-like and somewhat orris-like aroma. The compound having the structure:

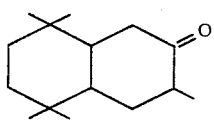

is commercially sold as "KETONE BD-9".

The compounds having the structure:

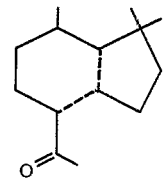

wherein one of the dashed lines represents a carbon-carbon double bond and the other of the dashed lines represents a carbon-carbon single bond is disclosed as being useful in perfumery (having a wood or ambergris aroma) in Japanese Published Patent No. 57-53768 assigned to the Takasago Perfumery Company.

The compound having the structure:

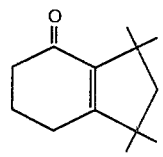

is disclosed as being useful in perfumery in U.S. Pat. No. 3,847,993 issued on Nov. 12, 1974. This compound is indicated to be produced using the compound having the structure:

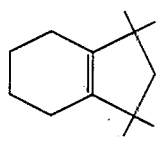

as a precursor according to the reaction:

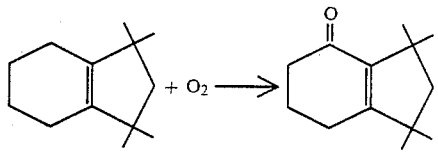

The compound having the structure:

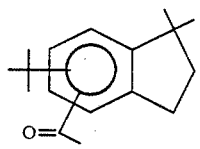

is disclosed as being useful in perfumery by Ferrero and Heig, Helv. Chim. Act. Volume XVII, Fasc. VI (1959) Number 228 at page 2111. This compound having the structure:

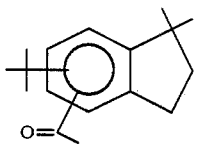

is produced from the compound having the structure:

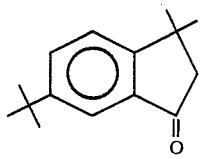

which is indicated to be an intermediate. Furthermore, in Ferrero and Heig, the compound having the structure:

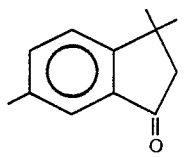

is indicated to be an intermediate for producing acylated indanes from the compound having the structure:

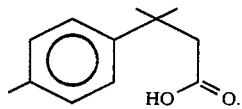

The compound having the structure:

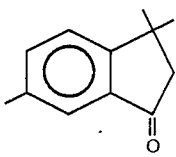

is indicated as compound XXIX. The compound having the structure:

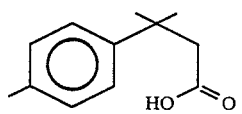

is indicated as compound XXVIII in Example C-3 at page 2119 of Ferrero and Heig.

Furthermore, the reaction:

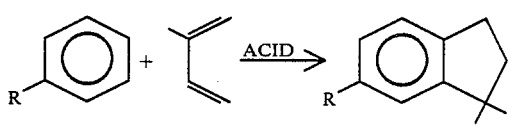

wherein R is lower alkyl such as methyl is disclosed in U.S. Pat. No. 3,078,319 issued on Feb. 19, 1963 wherein it is indicated that the resulting indanes may be acylated.

In addition, the use of cobolt acetate bromide and oxygen for the production of ketones is shown by Hay, et al, in the Canadian Journal of Chemistry, 43, 1306 (1965). In this process, tetralin is oxidized to the corresponding ketone, that is α-tetralone.

Nothing in the prior art, however, indicates the unexpected, unobvious and advantageous properties of the compound having the structure:

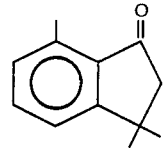

Furthermore, nothing in the prior art indicates the perfumery uses of the compounds having the structures:

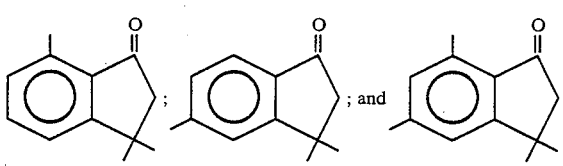

as covered by the genus having the structure:

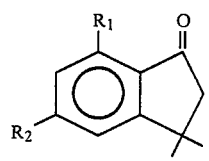

wherein $R_1$ and $R_2$ are the same or different and each represents hydrogen or methyl with the proviso that at least one of $R_1$ and $R_2$ is methyl. The compounds having the structures:

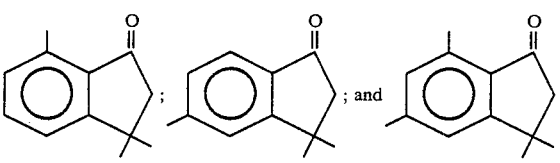

are novel compounds.

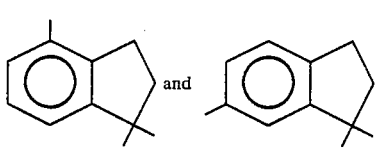

Figure 2:
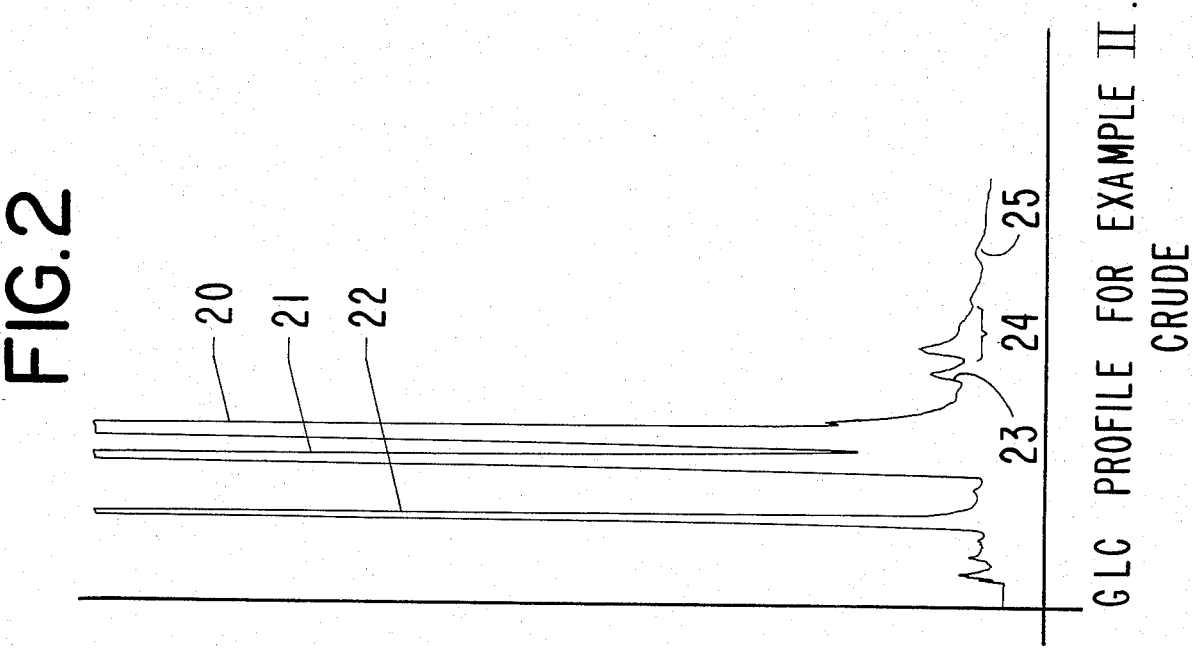

FIG. 2 is the GLC profile for the crude reaction product of Example II containing the compounds having the structures:

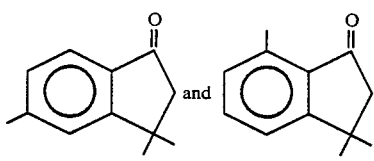

FIG. 3 is the NMR spectrum for fraction 3 of the distillation of Example II, for the compound having the structure:

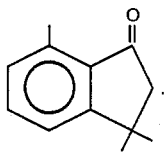

This NMR spectrum is for a GLC peak corresponding to the peak indicated by Reference Numeral 21 of FIG. 2. (Conditions: Field strength: 100 MHz; solvent: CFCl₃).

FIG. 4 is the NMR spectrum for fraction 3 of the distillation of the reaction product of Example II for the compound having the structure:

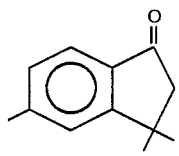

This spectrum is for a GLC peak corresponding to the peak indicated by Reference Numeral 22 of FIG. 2. (Conditions: Field strength: 100 MHz; solvent: CFCl₃).

FIG. 5 is the infra-red spectrum for fraction 3 of the distillation of the reaction product of Example II for the compound having the structure:

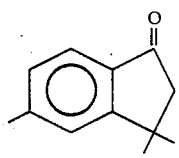

The infra-red spectrum is for a GLC peak which corresponds to the peak indicated by Reference Numeral 22 of FIG. 2.

Figure 6:
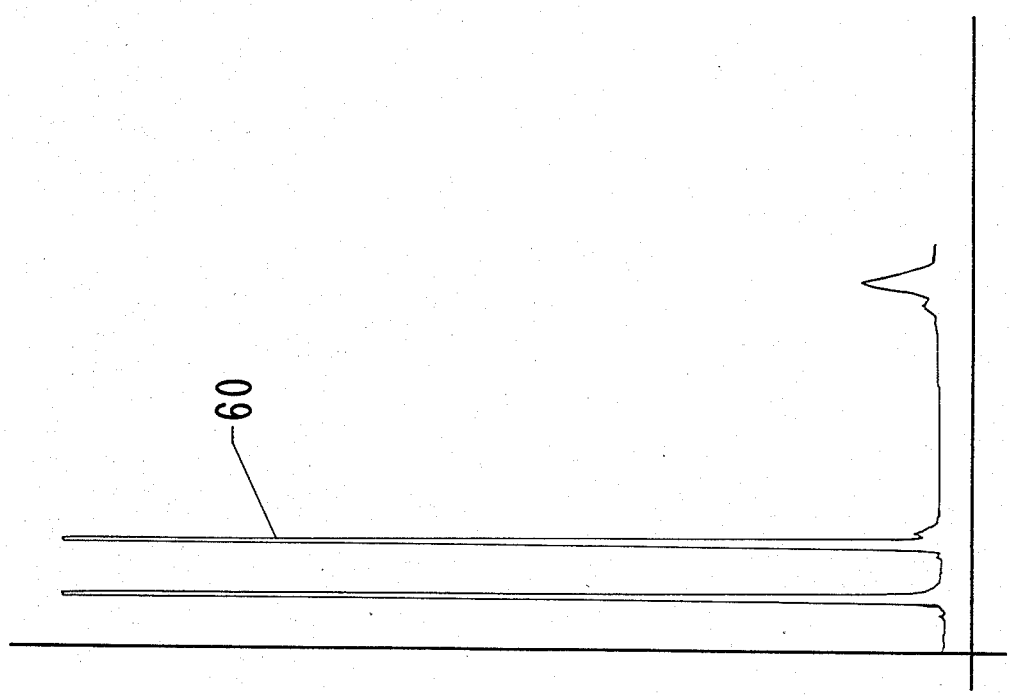

FIG. 6 is the GLC profile for the crude reaction product of Example III containing the compound having the structure:

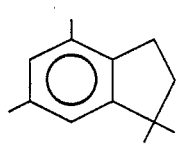

Figure 7:
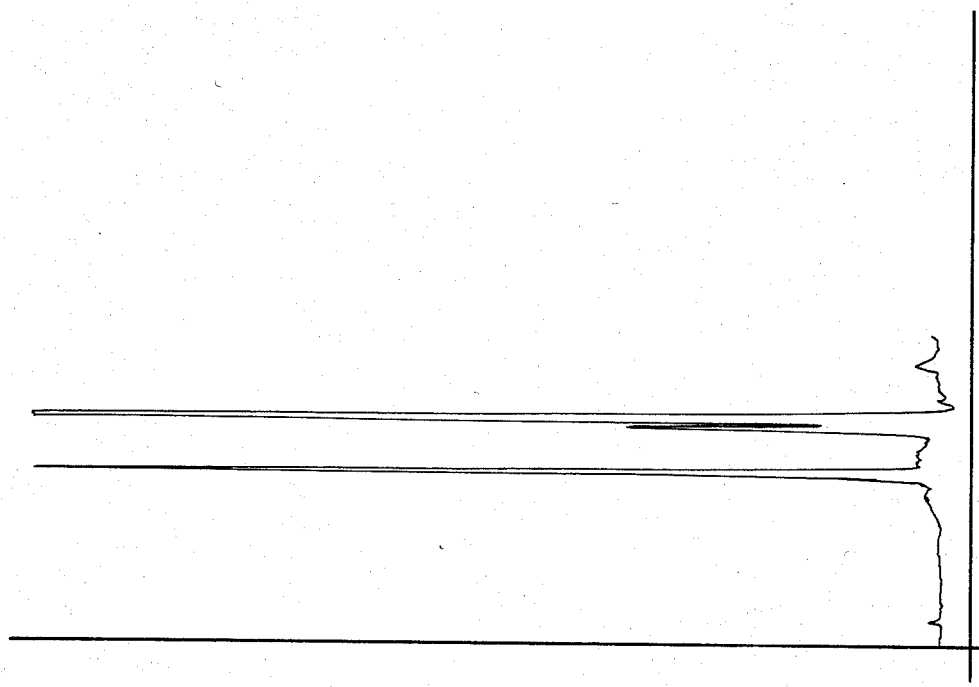

FIG. 7 is the GLC profile for the crude reaction product of Example IV containing the compound having the structure:

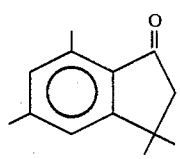

Figure 8:
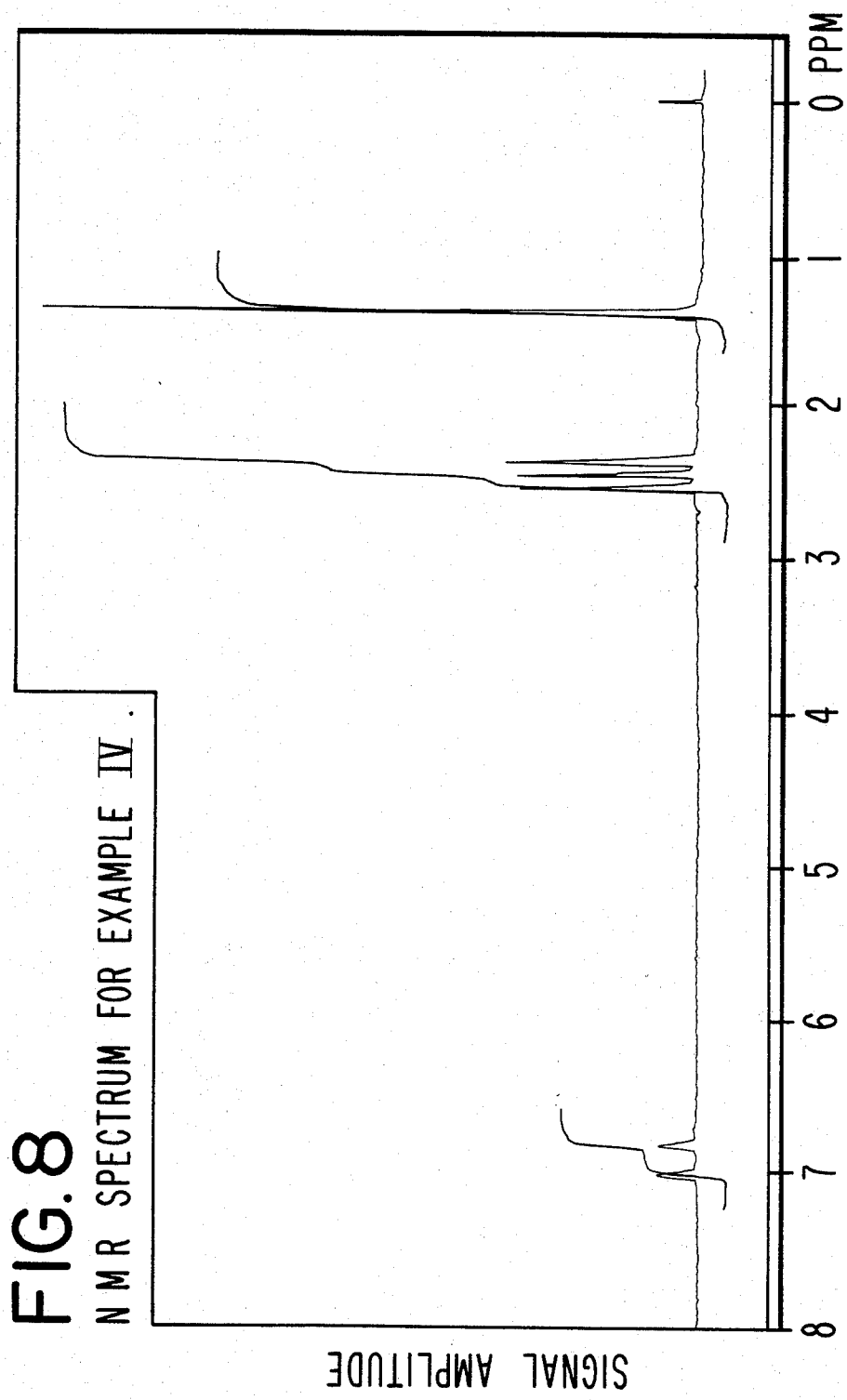

FIG. 8 is the NMR spectrum for the compound having the structure:

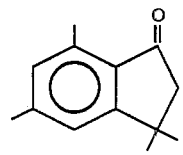

prepared according to Example IV. (Conditions: Field strength: 100 MHz; solvent: CFCl₃).

Figure 9:
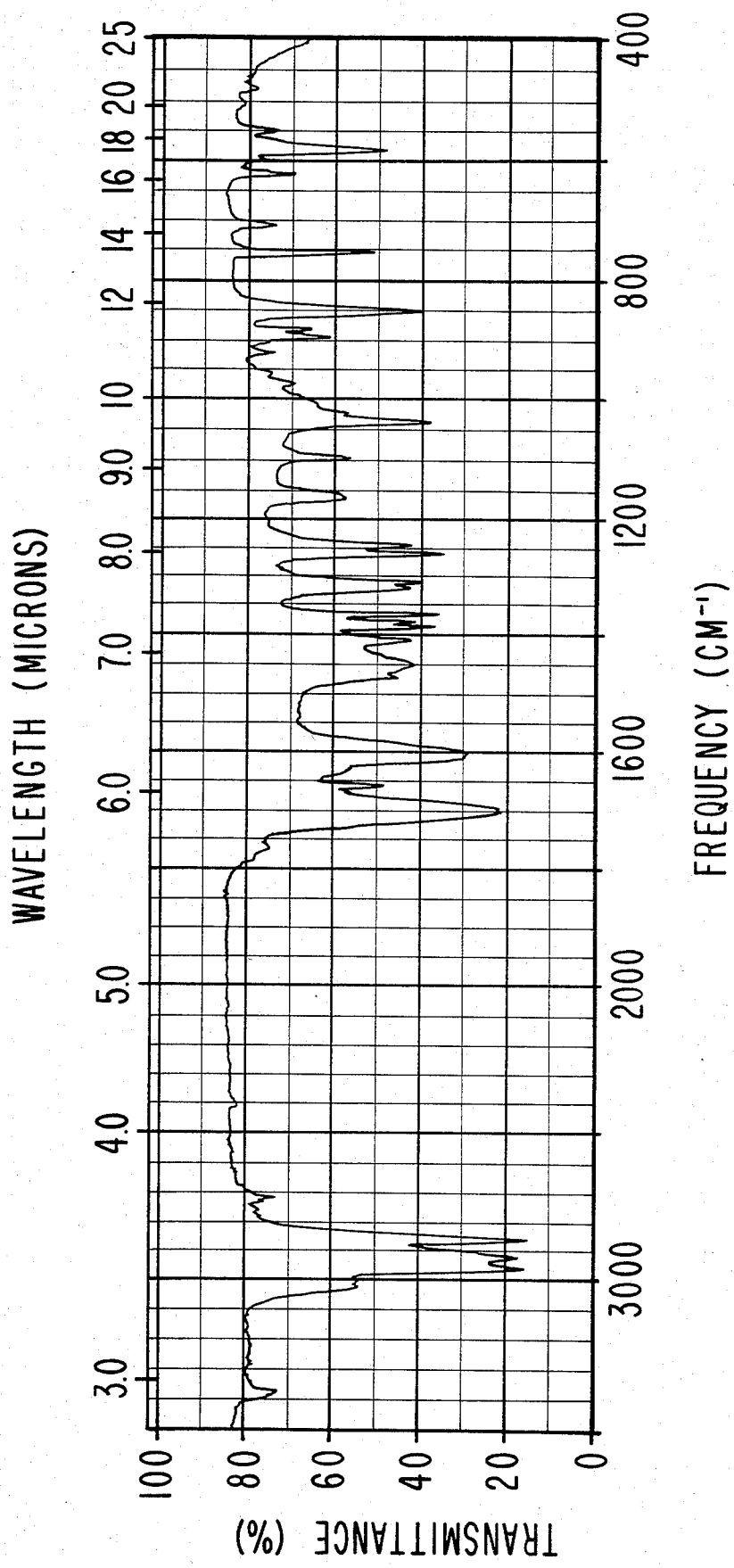

FIG. 9 is the infra-red spectrum for the compound produced according to Example IV having the structure:

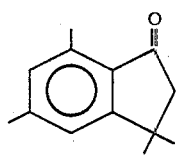

DETAILED DESCRIPTION OF THE DRAWINGS

FIG. 2 is the GLC profile for the crude reaction product of Example II. The peak indicated by Reference Numeral 20 is the peak for the compound having the structure:

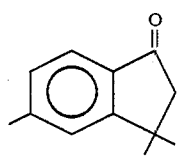

The peak indicated by Reference Numeral 21 is the peak for the compound having the structure:

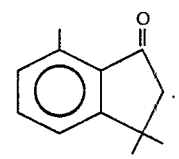

The peak indicated by Reference Numeral 22 is the peak for the unreacted indanes having the structures:

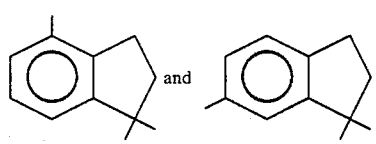

The peak indicated by Reference Numeral 23 is the peak for the side product defined according to the structure:

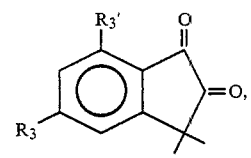

defining a mixture, wherein in the mixture one of $R_3$ or $R_3'$ is methyl and the other of $R_3$ or $R_3'$ is hydrogen.

The peaks indicated by Reference Numeral 24 are for the compounds having the structures:

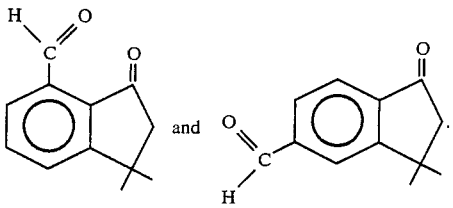

The peak indicated by Reference Numeral 25 is for the compounds having the structures:

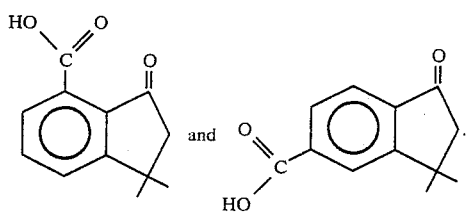

FIG. 6 is the GLC profile for the crude reaction product of Example III. The peak indicated by Reference Numeral 60 is the peak for the compound defined according to the structure:

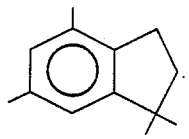

THE INVENTION

The present invention provides compounds defined according to the generic structure:

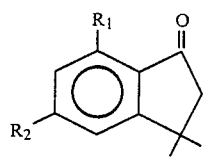

wherein $R_1$ and $R_2$ are the same or different and each represents methyl or hydrogen with the proviso that at least one of $R_1$ and $R_2$ is methyl.

The composition of matter of our invention produced according to the process of our invention is capable of augmenting, enhancing or providing leathery, amber, honey-like, orange flower-like, saffron-like, dried fruit, tobacco, woody, fruity and ozoney aromas with leathery, amber or orange flower absolute-like topnotes to perfume compositions, colognes and perfumed articles (e.g., solid or liquid anionic, cationic, nonionic or zwitterionic detergents, fabric softener articles, drier-added fabric softener articles, fabric softener compositions, cosmetic powders, hair preparations and perfumed polymers and the like).

The substances of our invention are first prepared by reacting toluene or meta-xylene with isoprene in the presence of an acidic catalyst, e.g., sulfuric acid, to form a tri or tetra methyl indane defined according to the generic structure:

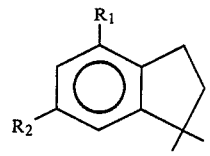

wherein $R_1$ and $R_2$ are the same or different and each represents hydrogen or methyl with the proviso that at least one of $R_1$ and $R_2$ is methyl, according to the reaction:

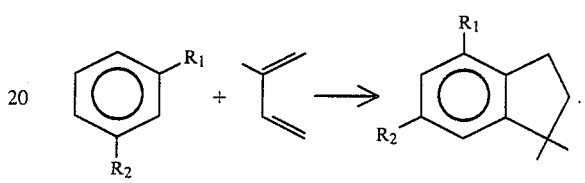

The parameters for this reaction are set forth in U.S. Pat. No. 3,078,319 issued on Feb. 19, 1963, the specification for which is incorporated by reference herein.

The resulting indane derivative defined according to the structure:

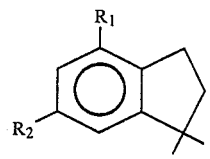

is then reacted with oxygen using an appropriate catalyst in order to form the 1,1-dimethyl-3-indanones of our invention defined according to the structure:

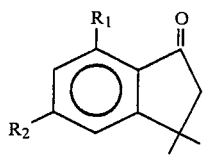

wherein $R_1$ and $R_2$ are defined, supra, according to the reaction:

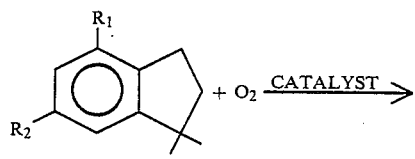

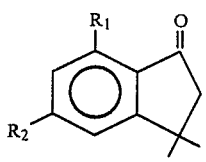

In fact, the reaction can be carried out using oxygen or air.

The reaction temperature may be in the range of from about 25° C. up to about 150° C. at a pressure of from about 1 atmosphere up to about 10 atmospheres. The reaction takes place in the presence of a solvent such as acetic acid, or benzene or in the absence of a solvent. The reaction takes place using a catalyst, such as cobolt naphthenate, cobolt acetoacetate or cobolt diacetate. Other transition metal (e.g., chromium maganese and copper) catalysts may also be used and these transition metal catalysts are the standard oxidation catalysts.

The reaction may be also carried out using air rather than oxygen. When using air as a reactant, the indane derivative defined according to the structure:

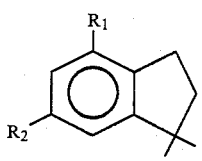

is charged into an autoclave with the appropriate catalyst, preferably a cobolt salt, such as cobolt aceto acetate.

The amount of catalyst used in the oxidation reaction may be from about 0.1% up to about 1% by weight of the reaction mass.

When using air, the air is introduced into the autoclave at a set velocity, preferably about 500 cc per minute. Preferably, when using air the reaction pressure may vary from about 50 up about 500 psig, more preferably between about 100 and 200 psig.

Examples of reaction products of our invention and their organoleptic properties are set forth in the following table:

TABLE I

| SUBSTANCE | AROMA DESCRIPTION |
|---|---|
| Compound having the structure: (prepared according to Example IV.) | A leathery, amber aroma with leathery topnotes. |
| Mixture of compounds having the structures: and (prepared according to Example II.) | A leathery, honey, orange flower, saffron-like aroma with amber and orange flower absolute-like topnotes. |

TABLE I-continued

| SUBSTANCE | AROMA DESCRIPTION |
|---|---|
| The compound having the structure: (prepared according to Example II.) | A dried fruit, honey, tobacco-like, woody, saffron-like, orange flower absolute-like aroma. |
| Compound having the structure: (prepared according to Example II.) | A woody, fruity, honey, ozoney aroma. |

One or more of the 1,1-dimethyl-3-indanones prepared in accordance with the process of our invention and one or more auxiliary perfume ingredients including, for example, alcohols, aldehydes, ketones other than the 1,1-dimethyl-3-indanones of our invention, turpenic hydrocarbons, nitriles, esters, lactones, natural essential oils and synthetic essential oils may be admixed so that the combined odors of the individual components produce a pleasant and desired fragrance, particularly and preferably in leathery, amber, spicy, vetiver-like, "chypre" and patchouli fragrances. Such perfume compositions usually contain:

(a) the main note or the "bouquet" or foundation stone of the composition;
(b) modifiers which round-off and accompany the main note;
(c) fixatives which include odorous substances which lend a particular note to the perfume throughout all stages of evaporation and substances which retard evaporation; and
(d) topnotes which are usually low boiling fresh smelling materials.

In perfume compositions, it is the individual components which contribute their particular olfactory characteristics, however, the overall sensory effect of the perfume composition will be at least the sum total of the effects of each of the ingredients. Thus, the 1,1-dimethyl-3-indanones prepared in accordance with the process of our invention can be used to alter, modify or enhance the aroma characteristics of a perfume composition, for example, by utilizing or moderating the olfactory reaction contributed by another ingredient in the composition.

The amount of the 1,1-dimethyl-3-indanones prepared in accordance with the process of our invention which will be effective in perfume compositions as well as in perfumed articles (e.g., anionic, cationic, nonionic or zwitterionic detergents, soaps, fabric softener compositions, fabric softener articles and perfumed polymers) and colognes depends upon many factors including the other ingredients, their amounts and the effects which are desired. It has been found that perfume compositions containing as little as 0.01% of the 1,1-dimethyl-3-indanones prepared in accordance with the process of our invention or even less (e.g., 0.005%) can be used to impart, augment or enhance leathery, amber, honey, orange flower, saffron-like, dried fruit, tobacco, woody, fruity and ozoney aromas with leathery, amber, orange flower absolute-like topnotes to soaps, cosmetics, anionic, cationic, nonionic or zwitterionic detergents, fabric softener compositions, fabric softener articles, microporous polymers, particularly acrylic resins, polyethylenes and other products. The amount employed can range up to 70% of the fragrance components and will depend on considerations of cost, nature of the end product, the effect desired on the finished product and the particular fragrance sought.

The 1,1-dimethyl-3-indanones prepared in accordance with the process of our invention are useful (taken alone or together with other ingredients in perfume compositions) as (an) olfactory component(s) in detergents and soaps, space odorants and deodorants, perfumes, colognes, toilet water, bath preparations such as creams, deodorants, hand lotions and sun screens; powders, such as talcs, dusting powders, face powders, microporous "perfumed" slow reease polymers and the like.

When used as (an) olfactory component(s) in perfumed articles, as little as 0.005% of the 1,1-dimethyl-3-indanones prepared in accordance with the process of our invention will suffice to impart, augment or enhance leathery, amber, honey, orange flower, saffron-like, dried fruit, tobacco, woody, fruity and ozoney aromas with leathery, amber and orange flower absolute-like topnotes. Generally, no more than 6% of the 1,1-dimethyl-3-indanones of our invention based on the ultimate end product is required in the perfumed article. Accordingly, the range of use of the 1,1-dimethyl-3-indanones of our invention in perfumed articles, per se, is from about 0.005% up to about 6% by weight based on the perfumed article.

In addition, the perfume composition or fragrance composition of our invention can contain a vehicle or carrier for the 1,1-dimethyl-3-indanones prepared in accordance with the process of our invention. The vehicle can be a liquid such as a non-toxic alcohol, e.g., ethyl alcohol, a non-toxic glycol, e.g., propylene glycol or the like. The carrier can also be an absorbent solid such as a gum (e.g., gum arabic, guar gum or xanthan gum or combination thereof) or components for encapsulating the composition (such as gelatin as by coacervation) or polymers such as urea formaldehyde prepolymers which form a urea formaldehyde polymer capsule wall around a liquid perfume scentor.

It will thus be apparent that the 1,1-dimethyl-3-indanones prepared in accordance with the process of our invention can be utilized to alter, modify or enhance sensory properties particularly organoleptic properties such as fragrances of a wide variety of consumable materials.

The following Examples I-IV set forth means for preparing the 1,1-dimethyl-3-indanones of our invention. The Examples following Example IV, Example V et seq, set forth illustrations of organoleptic utilities of the 1,1-dimethyl-3-indanones of our invention.

All parts and percentages given herein are by weight unless otherwise specified.

EXAMPLE I

Preparation of 1,1,6-Trimethyl Indane and 1,1-Trimethyl Indane Mixture

Reaction:

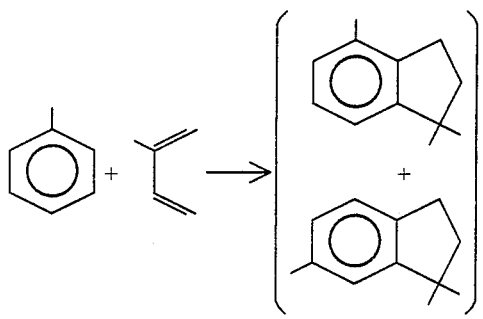

Into a 22 liter reaction vessel equipped with stirrer, thermometer, reflux condenser and heating mantle is placed 12 kilograms of sulfuric acid and 1.2 kilograms of water. The mixture is cooled to 10° C. To the resulting mixture is added 3.0 kilograms of toluene while maintaining the temperature of the mixture at 15°-20° C. Over a period of four hours, while maintaining the reaction temperature at 15°-20° C., with stirring, a mixture of 4.36 kilograms of toluene and 1.099 kilograms of isoprene is added to the reaction mass.

At the end of the four hour addition period, the reaction mass is stirred for an additional 15 minutes and the organic phase is separated from the aqueous phase. The organic phase is washed with saturated sodium chloride and then neutralized with 50% caustic.

The resulting product is then distilled on a fractional distillation column yielding the following fractions:

| FRACTION NO. | VAPOR TEMP. (°C.) | LIQUID TEMP. (°C.) | VACUUM mm/Hg PRESSURE |
| --- | --- | --- | --- |
| 1 | 42 | 52 | 200 |
| 2 | 55 | 55 | 200 |
| 3 | 55 | 68 | 200 |
| 4 | 57 | 75 | 200 |
| 5 | 57 | 84 | 200 |
| 6 | 57 | 84 | 200 |
| 7 | 88 | 122 | 100 |
| 8 | 103 | 112 | 50 |
| 9 | 103 | 112 | 50 |
| 10 | 100 | 112 | 50 |
| 11 | 100 | 112 | 50 |
| 12 | 100 | 112 | 30 |
| 13 | 92 | 116 | 30 |
| 14 | 95 | 120 | 30 |
| 15 | 95 | 153 | 25 |
| 16 | 88 | 160 | 22 |
| 17 | 110 | 180 | 1.2 |

Figure 1:
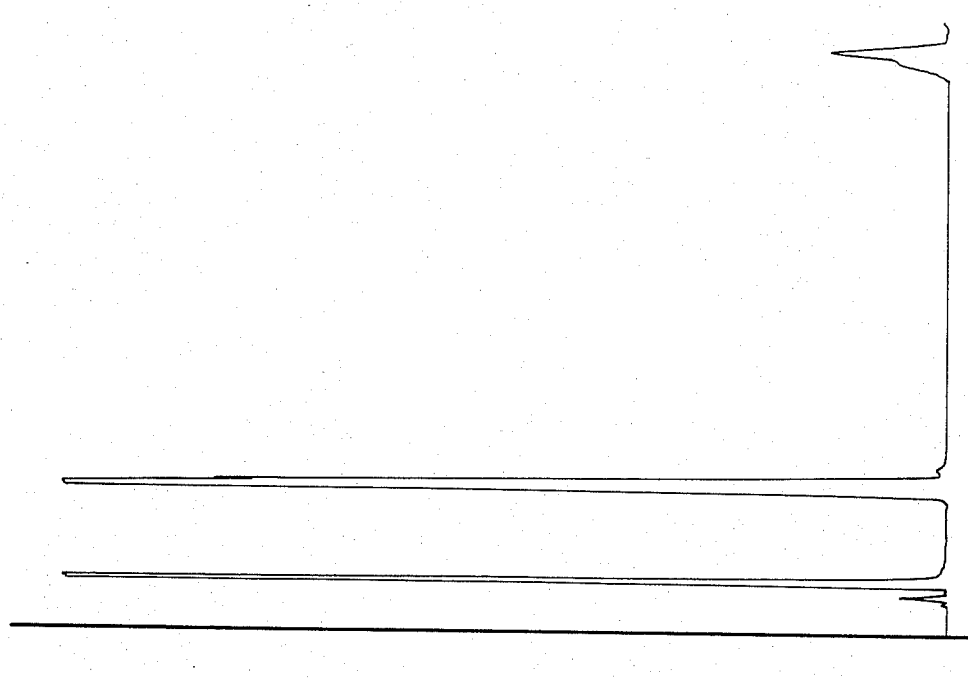
FIG. 1 is the GLC profile for the crude reaction product of Example I containing the compounds having the structures.

FIG. 1 is the GLC profile for the crude reaction product (Conditions: SE-30 column programmed at 180° C. isothermal).

EXAMPLE II

Preparation of Trimethyl Indanones

Reaction:

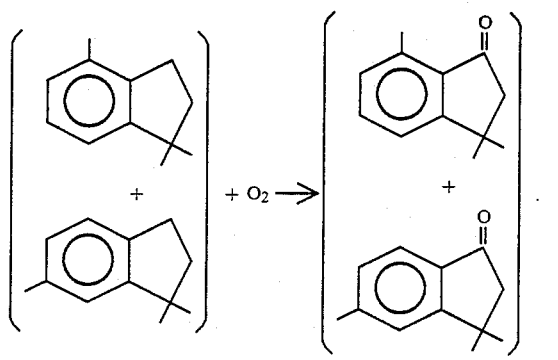

Into a 500 ml. "zipperclave" (high pressure autoclave) apparatus is placed 250 grams of the mixture of trimethyl indanes prepared in accordance with Example I having the structures:

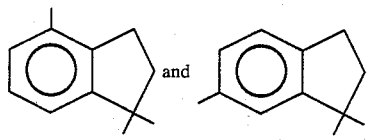

and in addition, 2 grams of chromium aceto acetate and 2 grams of cobolt acetoacetate. The autoclave is sealed and pressurized to 100 psig at a 500 ml. per minute oxygen flow rate with oxygen. The reaction temperature is maintained at 64°–83° C. for a period of 9 hours.

At the end of the nine hour period, GLC analysis indicates 85% completion of the reaction. The autoclave is cooled to room temperature, opened and the contents are filtered and subjected to a distillation on a 2″ splash column yielding 193 grams of product distilling at 65°–128° C. vapor temperature at 3 mm/Hg pressure and 95°–167° C. liquid temperature. The resulting product is then redistilled on a 12″×1.5″ Goodloe column yielding the following fractions:

| FRACTION NO. | VAPOR TEMP. (°C.) | LIQUID TEMP. (°C.) | VACUUM mm/Hg. PRESSURE |
|---|---|---|---|
| 1 | 85 | 108 | 1.0 |
| 2 | 85 | 109 | 1.0 |
| 3 | 92 | 115 | 3.0 |
| 4 | 92 | 115 | 3.0 |
| 5 | 92 | 115 | 3.0 |
| 6 | 92 | 115 | 3.0 |
| 7 | 90 | 115 | 3.0 |
| 8 | 90 | 115 | 3.0 |
| 9 | 90 | 115 | 3.0 |
| 10 | 90 | 115 | 3.0 |
| 11 | 90 | 120 | 3.0 |
| 12 | 90 | 140 | 3.0 |

FIG. 2 is the GLC profile for the crude reaction product containing the compounds having the structures:

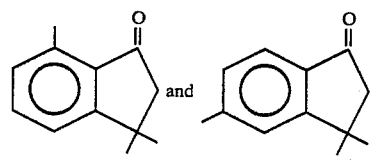

The peak indicated by Reference Numeral 20 is the peak for the isomer defined according to the structure:

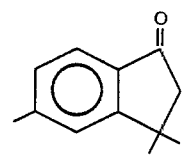

The peak indicated by Reference Numeral 21 is the peak for the isomer having the structure:

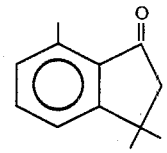

Each of these peaks is separated using commercial GLC preparative chromatography (SE-30 column programmed at 200° C. isothermal).

The peak indicated by Reference Numeral 22 is the peak for the unreacted indanes defined according to the structures:

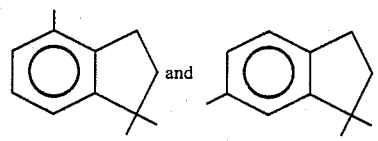

The peak indicated by Reference Numeral 23 is the peak for two compounds, diketone by-products defined according to the structure:

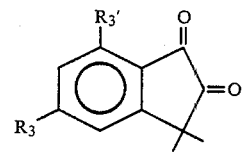

where $R_3'$ and $R_3$ are different and one represents methyl and the other represents hydrogen. The peaks indicated by Reference Numeral 24 is for the two compounds which are by-products having the structures:

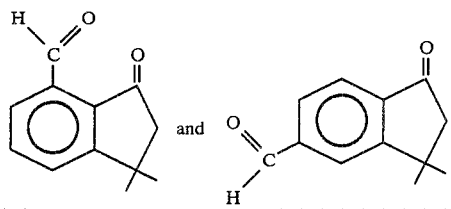

The peak indicated by Reference Numeral 25 is for the two by-products having the structures:

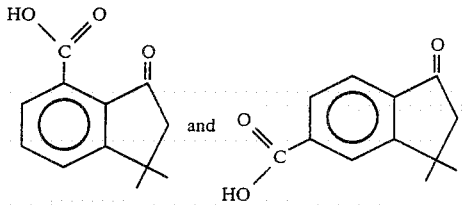

The compound having the structure:

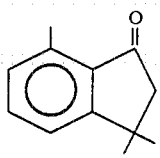

has unexpected, unobvious and advantageous properties; a dry fruit, honey-like, tobacco-like, woody, saffron-like, orange flower absolute-like aroma. The compound having the structure:

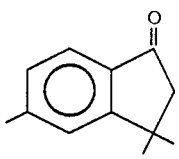

has a woody, fruity, honey and ozoney aroma. The compound having the structure:

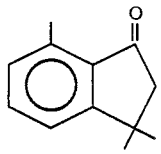

is ten times as strong as the compound having the structure:

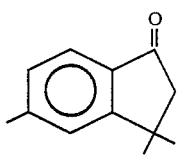

and has a lasting power ten times as long as the compound having the structure:

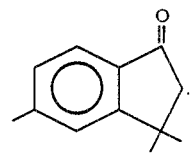

Furthermore, bulked fractions 5-11 of the foregoing distillation containing the compounds having the structures:

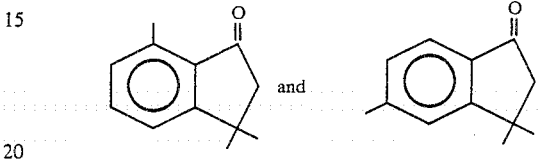

in admixture has a strong leathery, honey, orange flower, saffron-like aroma with amber and orange flower absolute-like topnotes causing it to be highly useful in chypre, leather, men's after shave formulations.

FIG. 3 is the NMR spectrum for the compound having the structure:

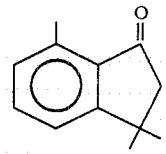

produced as a result of the GLC trapping of the compound from fraction 3 of the distillation of the reaction product of Example II. The peak indicated by the Reference Numeral 21 on FIG. 2 is the peak for the compound having the structure:

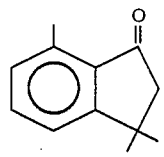

(Conditions: Field strength: 100 MHz; solvent: $CFCl_3$).

FIG. 4 is the NMR spectrum for the compound having the structure:

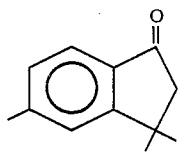

which is a GLC trap of fraction 3 of the distillation of the reaction product of Example II. The peak indicated by Reference Numeral 22 on FIG. 2 is the peak for the compound having the structure:

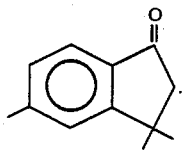

The conditions for the NMR: Field strength: 100 MHz; solvent: CFCl₃.

FIG. 5 is the infra-red spectrum for the compound having the structure:

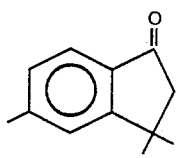

isolated from the GLC trapping of fraction 3 of the distillation of the reaction product of Example II. The peak indicated by Reference Numeral 22 on FIG. 2 is the peak for the compound having the structure:

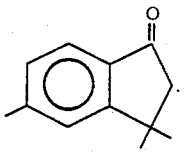

EXAMPLE III

Preparation of 1,1,4,6-Pentamethyl Indane

Reaction:

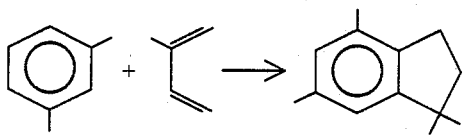

Into a 12 liter reaction vessel equipped with stirrer, thermometer, reflux condenser and heating mantle and cooling coils is placed 128 grams of water followed by 1.28 kilograms of concentrated sulfuric acid. The resulting mixture is cooled to 15° C. and 4.0 kilograms of m-xylene is added over a period of 15 minutes. While maintaining the reaction mass at 15° C., over a period of 4.25 hours, a mixture of 4.4936 kilograms of m-xylene and 1.088 kilograms of isoprene is added to the reaction mass. At the end of the feeding of the mixture of m-xylene and isoprene, the reaction mass is stirred for another 15 minutes while maintaining the reaction mass at 15° C.

The organic phase is then separated from the aqueous phase and the organic phase is neutralized with 50% caustic. The resulting material (1.647 kilograms) is then distilled yielding the following fractions:

| FRACTION NO. | VAPOR TEMP. (°C.) | LIQUID TEMP. (°C.) | VACUUM mm/Hg. PRESSURE |
|---|---|---|---|
| 1 | 77 | 85 | 200 |

-continued

| FRACTION NO. | VAPOR TEMP. (°C.) | LIQUID TEMP. (°C.) | VACUUM mm/Hg. PRESSURE |
|---|---|---|---|
| 2 | 77 | 85 | 200 |
| 3 | 78 | 93 | 200 |
| 4 | 77 | 103 | 200 |
| 5 | 64 | 112 | 200 |
| 6 | 95 | 122 | 150 |
| 7 | 114 | 122 | 50 |
| 8 | 110 | 120 | 30 |
| 9 | 108 | 110 | 20 |
| 10 | 95 | 150 | 4 |

FIG. 6 is the GLC profile for the crude reaction product containing the compound having the structure:

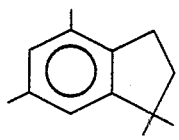

The peak indicated by Reference Numeral 60 is the peak for the compound having the structure:

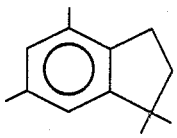

EXAMPLE IV

Production of 1,4,6-Tetramethyl-3-Indanone

Reaction:

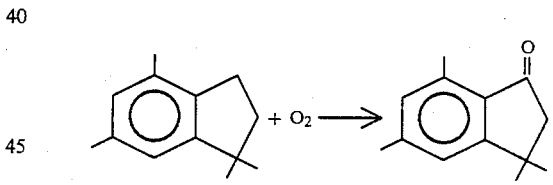

Into a 500 cc zipperclave (pressure autoclave) is placed 300 grams of the indane having the structure:

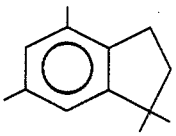

and 1.5 grams of cobolt acetoacetate. The autoclave is sealed and pressurized with oxygen to 100 psig (oxygen flow rate: 500 ml. per minute). The contents of the autoclave are heated between 96° and 111° C. for a period of 14 hours while maintaining the pressure at 100 psig and the oxygen flow rate at 500 ml. per minute. At the end of the 14 hour period, GLC analysis (conditions: SE-30 column programmed at 180° C., isothermal).

The autoclave is then cooled to room temperature, opened and the contents are removed and filtered. The filtrate is then washed with a 10% sodium hydroxide solution and distilled at a vapor temperature of 40°–70° C. and a liquid temperature of 60°–120° C. at 3–20 mm/Hg. pressure. This distillation takes place on a 2" splash column.

The resulting distillate is then redistilled on a 12"×1.5" fractional distillation column yielding the following fractions:

| FRACTION NO. | VAPOR TEMP. (°C.) | LIQUID TEMP. (°C.) | VACUUM mm/Hg. PRESSURE |
|---|---|---|---|
| 1 | 65–68 | 105–111 | 3.0 |
| 2 | 85 | 112 | 3.0 |
| 3 | 96 | 112 | 3.0 |
| 4 | 97 | 113 | 3.0 |
| 5 | 97 | 113 | 3.0 |
| 6 | 97 | 113 | 3.0 |
| 7 | 97 | 113 | 3.0 |
| 8 | 97 | 113 | 3.0 |
| 9 | 97 | 175 | 3.0 |

FIG. 7 is the GLC profile for the crude reaction product containing the compound having the structure:

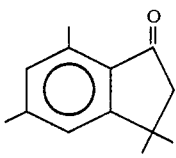

FIG. 8 is the NMR spectrum for the compound having the structure:

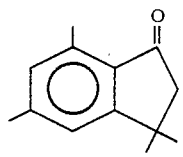

prepared according to this Example (Conditions: Field strength: 100 MHz; solvent: CFCl$_3$).

FIG. 9 is the infra-red spectrum for the compound having the structure:

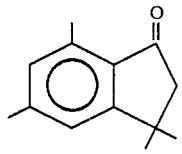

prepared according to this Example.

The resulting product having the structure:

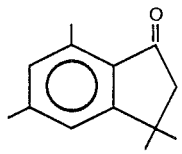

has an intense leathery amber aroma with leathery topnotes.

EXAMPLE V

The following chypre formulations are prepared:

| INGREDIENTS | PARTS BY WEIGHT | | | |
|---|---|---|---|---|
| | EXAMPLE V(A) | EXAMPLE V(B) | EXAMPLE V(C) | EXAMPLE V(D) |
| Musk ambrette | 40.0 | 40.0 | 40.0 | 40.0 |
| Musk ketone | 60.0 | 60.0 | 60.0 | 60.0 |
| Coumarin | 30.0 | 30.0 | 30.0 | 30.0 |
| Oil of bergamot | 150.0 | 150.0 | 150.0 | 150.0 |
| Oil of lemon | 100.0 | 100.0 | 100.0 | 100.0 |
| Methyl ionone | 50.0 | 50.0 | 50.0 | 50.0 |
| Hexyl cinnamic aldehyde | 100.0 | 100.0 | 100.0 | 100.0 |
| Hydroxycitronellal | 100.0 | 100.0 | 100.0 | 100.0 |
| Oil of lavender | 50.0 | 50.0 | 50.0 | 50.0 |
| Texas cedarwood oil | 85.0 | 85.0 | 85.0 | 85.0 |
| Virginia cedarwood oil | 30.0 | 30.0 | 30.0 | 30.0 |
| Oil of sandalwood (East Indies) | 40.0 | 40.0 | 40.0 | 40.0 |
| Isoeugenol | 20.0 | 20.0 | 20.0 | 20.0 |
| Eugenol | 10.0 | 10.0 | 10.0 | 10.0 |
| Benzyl acetate | 30.0 | 30.0 | 30.0 | 30.0 |
| β-phenyl ethyl alcohol | 40.0 | 40.0 | 40.0 | 40.0 |
| α-phenyl ethyl alcohol | 30.0 | 30.0 | 30.0 | 30.0 |
| Oakmoss absolute | 30.0 | 30.0 | 30.0 | 30.0 |
| Vetiver oil (Venezuela) | 25.0 | 25.0 | 25.0 | 25.0 |
| The compound having the structure: prepared according to Example IV | 8.0 | 0.0 | 0.0 | 0.0 |
| The mixture of compounds having the structures: and prepared according to Example II, bulked fractions 5 to 11 | 0.0 | 2.0 | 0.0 | 0.0 |
| The compound having the structure: | 0.0 | 0.0 | 0.5 | 0.0 |
| The compound having the structure: | 0.0 | 0.0 | 0.0 | 15.0 |

The compound having the structure:

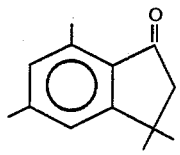

imparts to this chypre formulation leathery amber undertones and a leathery topnote. Accordingly, the perfume formulation of Example V(A) can be described as "chypre having an intense leathery and amber undertone with leathery topnotes".

The perfume formulation of Example V(B) can be described as "chypre, having leathery, honey, orange flower and saffron-like undertones with amber and orange flower absolute-like topnotes".

The perfume formulation of Example V(C) containing the compound having the structure:

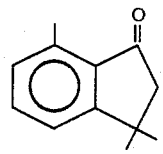

can be described as "chypre, with a dried fruit-like, honey-like, tobacco-like, woody, saffron-like and orange flower absolute-like undertone, highly intense and extremely long lasting".

The perfume formulation of Example V(D) containing the compound having the structure:

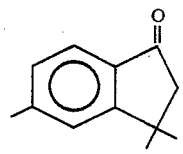

can be described as "chypre with a woody, fruity, honey and ozoney undertone".

EXAMPLE VI

Preparation of Cosmetic Powder Compositions

Cosmetic powder compositions are prepared by mixing in a ball mill 100 grams of talcum powder with 0.25 grams of each of the substances set forth in Table II below. Each of the cosmetic powder compositions has an excellent aroma as described in Table II below:

TABLE II

| SUBSTANCE | AROMA DESCRIPTION |
|---|---|
| The compound having the structure:<br />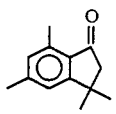 | A leathery amber aroma with leathery topnotes. |
| Mixture of compounds having the structures:<br /> and 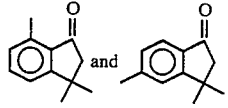<br />bulked fractions 5–11 of Example II | A leathery, honey, orange flower, saffron-like aroma with amber and orange flower absolute-like topnotes. |
| Pure compound having the structure:<br /><br />prepared according to Example II | An intense very long lasting dried fruit-like, honey, tobacco-like, woody, saffron-like and orange flower absolute-like aroma. |
| Compound having the structure:<br /><br />prepared according to Example II | A woody, fruity, honey and ozoney aroma. |
| Perfume composition of Example V(A) | Chypre having an intense leathery and amber undertone with leathery topnotes. |
| Perfume composition of Example V(B) | Chypre having leathery, honey, orange flower and saffron-like undertones with amber and orange flower absolute-like topnotes. |
| Perfume composition of Example V(C) | Chypre, with a dried fruit-like, honey-like, tobacco-like, woody, saffron-like and orange flower absolute-like undertone, highly intense and extremely long lasting. |
| Perfume composition of Example V(D) | Chypre with a woody, fruity, honey and ozoney undertone. |

EXAMPLE VII

Perfumed Liquid Detergents

Concentrated liquid detergents (Lysine salt of n-dodecylbenzene sulfonic acid as more specifically described in U.S. Pat. No. 3,948,818, issued on Apr. 6, 1976 incorporated by reference herein) with aroma nuances as set forth in Table II of Example VI, are prepared containing 0.10%, 0.15%, 0.20%, 0.25%, 0.30% and 0.35% of the substance set forth in Table II of Example VI. They are prepared by adding and homogeneously mixing the appropriate quantity of substance set forth in Table II of Example VI in the liquid detergent. The detergents all possess excellent aromas as set forth in Table II of Example VI, the intensity increasing with greater concentrations of substances as set forth in Table II of Example VI.

EXAMPLE VIII

Preparation of Colognes and Handkerchief Perfumes

Compositions as set forth in Table II of Example VI are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definitive fragrances as set forth in Table II of Example VI are imparted to the colognes and to the handkerchief perfumes at all levels indicated.

EXAMPLE IX

Preparation of Soap Compositions

One hundred grams of soap chips [per sample] (IVORY ®, produced by the Procter & Gamble Company of Cincinnati, Ohio), are each mixed with one gram samples of substances as set forth in Table II of Example VI until homogeneous compositions are obtained. In each of the cases, the homogeneous compositions are heated under 8 atmospheres pressure at 180° C. for a period of three hours and the resulting liquids are placed into soap molds. The resulting soap cakes, on cooling, manifest aromas as set forth in Table II of Example VI.

EXAMPLE X

Preparation of Solid Detergent Compositions

Detergents are prepared using the following ingredients according to Example I of Canadian Pat. No. 1,007,948 (incorporated by reference herein):

| INGREDIENT | PERCENT BY WEIGHT |
| --- | --- |
| "Neodol" ® 45-11 (a $C_{14}$-$C_{15}$ alcohol ethoxylanted with 11 moles of ethylene oxide) | 12 |
| Sodium carbonate | 55 |
| Sodium citrate | 20 |
| Sodium sulfate, water brighteners | q.s. |

This detergent is a phosphate-free detergent. Samples of 100 grams each of this detergent are admixed with 0.10, 0.15, 0.20 and 0.25 grams of each of the substances as set forth in Table II of Example VI. Each of the detergent samples has an excellent aroma as indicated in Table II of Example VI.

EXAMPLE XI

Utilizing the procedure of Example I at column 15 of U.S. Pat. No. 3,632,396 (the disclosure of which is incorporated herein by reference), nonwoven cloth substrates useful as drier-added fabric softening articles of manufacture are prepared wherein the substrate, the substrate coating, the outer coating and their perfuming material are as follows:
1. A water "dissolvable" paper ("Dissolvo Paper")
2. Adogen 448 (m.p. about 140° F.) as the substrate coating; and
3. An outer coating having the following formulation (m.p. about 150° F.):
57% $C_{20-22}$ HAPS
22% isopropyl alcohol
20% antistatic agent
1% of one of the substances as set forth in Table II of Example VI.

Fabric softening compositions prepared according to Example I at column 15 of U.S. Pat. No. 3,632,396 having the aroma characteristics as set forth in Table II of Example VI, supra, consist of a substrate coating having a weight of about 3 grams per 100 square inches of substrate; a first coating located directly on the substrate coating consisting of about 1.85 grams per 100 square inches of substrate; and an outer coating coated on the first coating consisting of about 1.4 grams per 100 square inches of substrate. One of the substances of Table II of Example VI is admixed in each case with the outer coating mixture, thereby providing a total aromatized outer coating weight ratio to substrate of about 0.5:1 by weight of the substrate. The aroma characteristics are imparted in a pleasant manner to the head space in a dryer on operation thereof in each case using said dryer-added fabric softener non-woven fabrics and these aroma characteristics are described in Table II of Example VI, supra.

EXAMPLE XII

Hair Spray Formulations

The following hair spray formulation is prepared by first dissolving PVP/VA E-735 copolymer manufactured by the GAF Corporation of 140 West 51st Street, New York, N.Y., in 91.62 grams of 95% food grade ethanol. 8.0 grams of the polymer is dissolved in the alcohol. The following ingredients are added to the PVP/VA alcoholic solution:

| INGREDIENT | PERCENT BY WEIGHT |
| --- | --- |
| Dioctyl sebacate | 0.05 |
| Benzyl alcohol | 0.10 |
| Dow Corning 473 fluid (prepared by the Dow Corning Corporation) | 0.10 |
| Tween 20 surfactant (prepared by ICI America Corporation) | 0.03 |
| One of the perfumery substances as set forth in Table II of Example VI, supra | 0.10 |

The perfuming substances as set forth in Table II of Example VI add aroma characteristics as set forth in Table II of Example VI which are rather intense and aesthetically pleasing to the users of the soft-feel, good-hold pump hair sprays.

EXAMPLE XIII

Conditioning Shampoos

Monamid CMA (prepared by the Mona Industries Company) (3.0 weight percent) is melted with 2.0 weight percent coconut fatty acid (prepared by Procter & Gamble Company of Cincinnati, Ohio); 1.0 weight percent ethylene glycol distearate (prepared by the Armak Corporation) and triethanolamine (a product of Union Carbide Corporation) (1.4 weight percent). The resulting melt is admixed with Stepanol WAT produced by the Stepen Chemical Company (35.0 weight percent). The resulting mixture is heated to 60° C. and mixed until a clear solution is obtained (at 60° C.). This material is "COMPOSITION A".

Gafquat ®755N polymer (manufactured by GAF Corporation of 140 West 51st Street, New York, N.Y.) (5.0 weight percent) is admixed with 0.1 weight percent sodium sulfite and 1.4 weight percent polyethylene glycol 6000 distearate produced by Armak Corporation. This material is "COMPOSITION B".

The resulting COMPOSITION A & COMPOSITION B are then mixed in a 50:50 weight ratio of A:B and cooled to 45° C. and 0.3 weight percent of perfuming substance as set forth in Table II of Example VI is added to the mixture. The resulting mixture is cooled to 40° C. and blending is carried out for an additional one hour in each case. At the end of this blending period, the resulting material has a pleasant fragrance as indicated in Table II of Example VI.

What is claimed is:

1. The indanone having the structure:

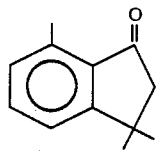

in recovered form.

2. A process for augmenting or enhancing the aroma of a consumable material selected from the group consisting of perfume compositions, colognes and perfumed articles comprising the step of adding to said consumable material an aroma augmenting or enhancing quantity of at least one 1,1-dimethyl-3-indanone defined according to the structure:

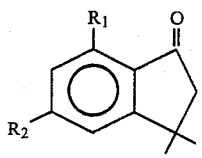

in recovered form wherein $R_1$ and $R_2$ are the same or different and each represents hydrogen or methyl with the proviso that at least one of $R_1$ or $R_2$ is methyl.

3. The process of claim 2 wherein the consumable material is a perfume composition or cologne.

4. The process of claim 2 wherein the consumable material is a perfumed article and the perfumed article is a perfumed polymer.

5. The process of claim 2 wherein the consumable material is a perfumed article and the perfumed article is a solid or liquid anionic, cationic, nonionic or zwitterionic detergent.

6. The process of claim 2 wherein the consumable material is a perfumed article and the perfumed article is a fabric softener composition or fabric softener article.

7. The product produced according to the process comprising the steps of (i) reacting the indane defined according to the structure:

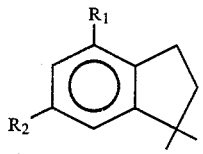

wherein $R_1$ and $R_2$ are each the same or different and each represents hydrogen or methyl with the proviso that at least one of $R_1$ or $R_2$ is methyl, with oxygen or air in the presence of a transition metal oxidation catalyst at a pressure of from about 1 atmosphere up to about 10 atmospheres and at a temperature in the range of from about 25° C. up to about 150° C., and (ii) recovering a fractional distillation product from the reaction mixture with the provisos that:

(a) when one of $R_1$ and $R_2$ is methyl then the distillation product is recovered at 90°–92° C. and 115–120 mm/Hg pressure; and (b) when both $R_1$ and $R_2$ are methyl then the distillation product is recovered at 96°–97° C. and 112–113 mm/Hg pressure.

8. The product of claim 7 wherein in the process for producing said product the reaction is carried out in the presence of a catalyst selected from the group consisting of cobalt acetoacetate, cobalt naphthenate and cobalt diacetate.

9. The product of claim 7 wherein in the process for producing said product the reaction is carried out using oxygen.

10. The product of claim 7 wherein in the process for preparing said product, the process is carried out in a solvent selected from the group consisting of acetic acid and benzene.

11. The product of claim 7 wherein in the process for preparing said product, the reaction is carried out in the absence of additional solvent.

12. The product of claim 7 wherein in the process for preparing said product, the indane defined according to the structure:

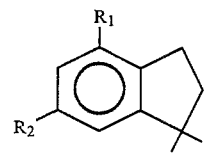

is prepared by reacting isoprene with a benzene derivative defined according to the structure:

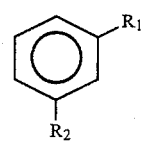

using a protonic acid catalyst.

13. A process for augmenting or enhancing the aroma of a consumable material selected from the group consisting of perfume compositions, colognes and perfumed articles comprising the step of adding to said consumable material, an aroma augmenting or enhancing quantity of the product of claim 7.

14. The process of claim 13 wherein the consumable material is a perfume composition or cologne.

15. The process of claim 13 wherein the consumable material is a perfumed article and the perfumed article is a perfumed polymer.

16. The process of claim 13 wherein the consumable material is a perfumed article and the perfumed article is a solid or liquid cationic, anionic, nonionic or zwitterionic detergent.

17. The process of claim 13 wherein the consumable material is a perfumed article and the perfumed article is a fabric softener composition or fabric softener article.

* * * * *